United States Patent
Fischell

(10) Patent No.: US 9,566,183 B1
(45) Date of Patent: Feb. 14, 2017

(54) NASAL STRIP HAVING END TABS TO ENHANCE THE REMOVAL OF THE NASAL STRIP FROM THE USER'S NOSE

(71) Applicant: Robert E. Fischell, Dayton, MD (US)

(72) Inventor: Robert E. Fischell, Dayton, MD (US)

( * ) Notice: Subject to any disclaimer, the term of this patent is extended or adjusted under 35 U.S.C. 154(b) by 0 days.

(21) Appl. No.: 15/216,122

(22) Filed: Jul. 21, 2016

Related U.S. Application Data

(63) Continuation-in-part of application No. 14/929,577, filed on Nov. 2, 2015, now Pat. No. 9,414,957, which is a continuation-in-part of application No. 14/468,881, filed on Aug. 26, 2014, now Pat. No. 9,204,988.

(51) Int. Cl.
 *A61F 5/08* (2006.01)

(52) U.S. Cl.
 CPC ..................... *A61F 5/08* (2013.01)

(58) Field of Classification Search
 CPC .............. A61F 5/08; A61F 5/56; A61B 1/233
 See application file for complete search history.

(56) References Cited

U.S. PATENT DOCUMENTS

| | | | | |
|---|---|---|---|---|
| 4,336,806 | A * | 6/1982 | Eldridge, Jr. | A61M 25/02 128/DIG. 26 |
| 9,204,988 | B1 * | 12/2015 | Fischell | A61F 5/08 |
| 9,414,957 | B1 * | 8/2016 | Fischell | A61F 5/08 |
| 2013/0060184 | A1 * | 3/2013 | Rea | A61F 13/0246 602/54 |
| 2013/0197569 | A1 | 8/2013 | Allen | |

* cited by examiner

*Primary Examiner* — Victor Nguyen
(74) *Attorney, Agent, or Firm* — Rosenberg, Klein & Lee

(57) ABSTRACT

A nasal strip for opening nasal passageways having an external portion formed from a plastic material that extends throughout the length of the nasal strip. The external portion has a central section and opposing end sections with the central section having the same or a smaller width as compared to the nasal strip width at each end section. An adhesive coating covers each of the end sections and the central section does not have an adhesive coating. A non-adhesive tab extending from either or both end sections provides a novel means for the easy removal of the nasal strip from the user's nose.

7 Claims, 2 Drawing Sheets

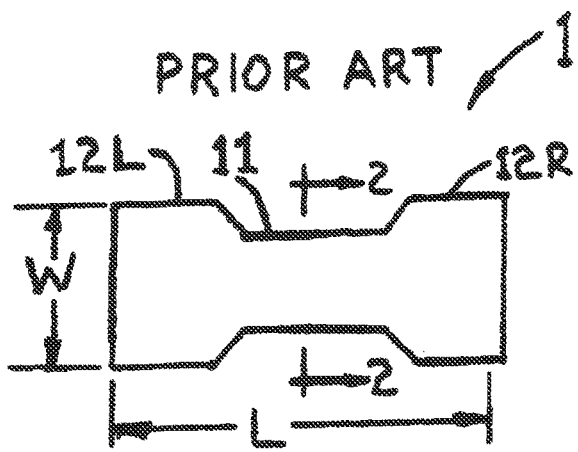
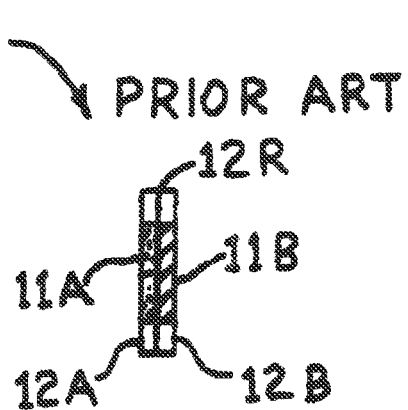
FIG. 1  FIG. 2
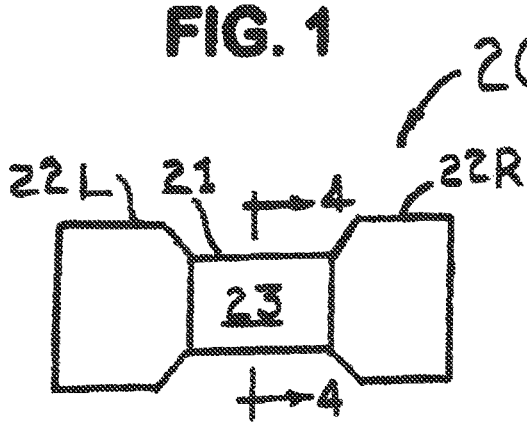
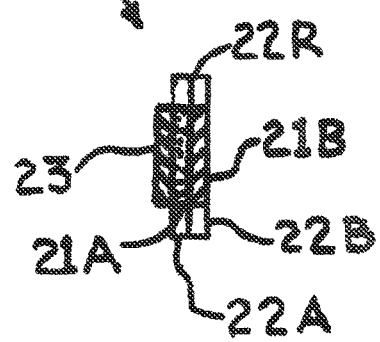
FIG. 3  FIG. 4
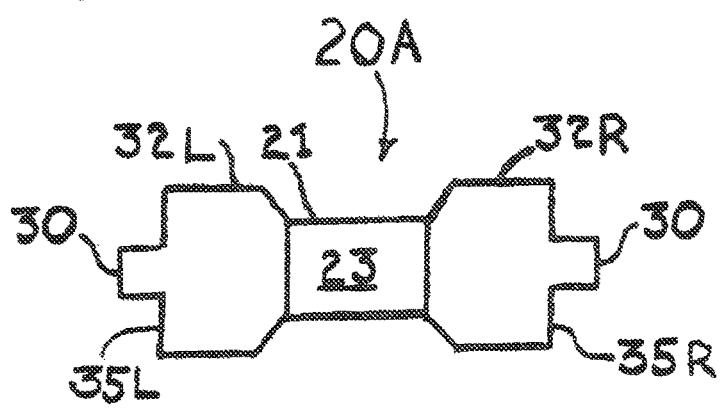
FIG. 5

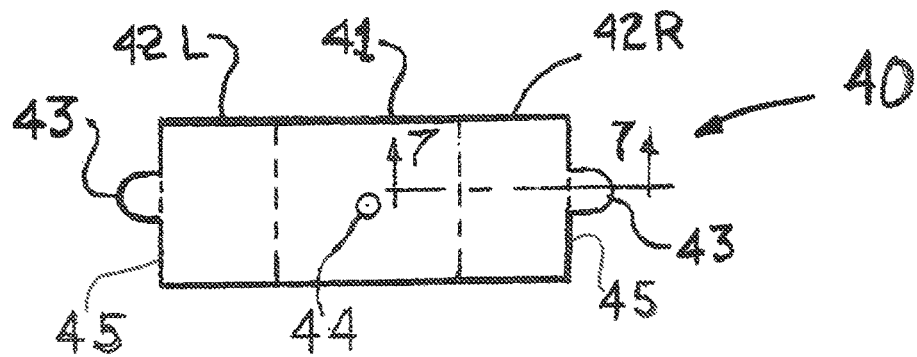
FIG. 6
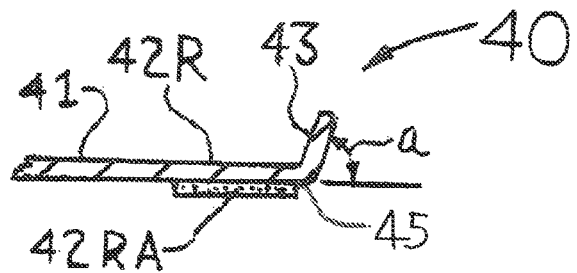
FIG. 7
FIG. 8
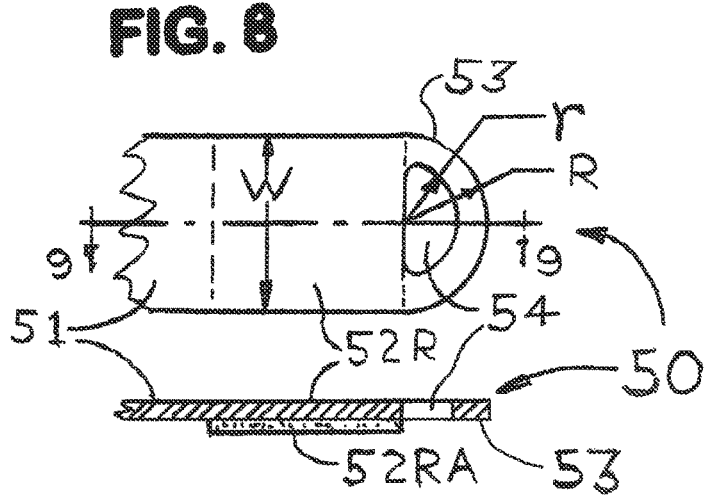
FIG. 9

NASAL STRIP HAVING END TABS TO ENHANCE THE REMOVAL OF THE NASAL STRIP FROM THE USER'S NOSE

REFERENCE TO RELATED APPLICATIONS

This Patent Application is a Continuation-in-Part of U.S. patent application Ser. No. 14/929,577 filed on 2 Nov. 2015, now Pending, which is a Continuation-in-Part of U.S. Pat. No. 9,204,988, issued on Dec. 8, 2015.

FIELD OF USE

This invention is in the field of devices to improve the opening of the nasal passageways.

BACKGROUND OF THE INVENTION

It is well known to use adhesive strips attached to the skin across the outside of the nose to improve the opening of the nasal passageways, particularly during sleep. One example of such a device is the Breathe Right® nasal strip which is a product of GlaxoSmithKline. However, that device has the disadvantage of only applying a moderate torque for opening the nasal passage and also, the adhesive attachment to the skin is so strong that there is some discomfort when that nasal strip is removed from the nose. Still further, there is sometimes an irritation of the skin on the nose when this nasal strip is repeatedly used for a number of consecutive days or nights.

Therefore, any nasal strip that could have: 1) more torque applied to open the nasal passageway, 2) less discomfort when the nasal strip is removed, 3) easier means for holding the nasal strip for placement onto the nose, 4) a tab at each end of the nose strip that is free of adhesive to make it easier to remove the nasal strip from that person's nose and 5) a decrease in the area of the skin that could be irritated by the adhesive attached to the skin would all constitute improvements in the design of such devices.

SUMMARY OF THE INVENTION

The present invention is a novel and useful means to improve the characteristics of nasal strips by the placement of a non-adhesive central portion situated between the two adhesive end sections of the nasal strip. For example, a thin plastic covering over the adhesive surface of the central portion of a nasal strip or merely the elimination of an adhesive on the central portion of the nasal strip can provide four advantages of: (1) more torque obtained to open the nasal passageway, (2) less discomfort on removal of the nasal strip, (3) easier means for placement of the nasal strip onto the nose and, (4) less area of the skin on the nose that can be irritated by the adhesive interior surface of the nasal strip. Another means to improve the lifting torque of a nasal strip is to have a central portion of the nasal strip that is as wide as the end sections of the nasal strip, without any adhesive on that central portion.

Thus one object of the present invention is to increase the torque applied by a nasal strip to improve the opening of the nasal passageways.

Another object of this invention is to decrease the user's discomfort when removing the nasal strip from his/her nose.

Still another object of this invention is to have a central region of the nasal strip that does not have an adhesive surface so that it is more easily held when placing the nasal strip onto the nose.

Still another object of this invention is decrease the area of the skin that can be irritated by the application of the nasal strip for many hours, particularly during sleep.

Still another object of this invention is to gain additional lifting toque for the side portions of the nose by having a central portion of the nasal strip that is as wide as the end sections of the nasal strip which is an advantage compared to all existing nasal strips that have a narrow central portion so as to decrease the irritation of the bridge of the nose.

Still another advantage of this invention is to have adhesive-free tabs attached to the ends of the nasal strip end sections to provide an easier means for removing the nasal strip from the user's nose.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1 is a plan view of a prior art nasal strip.

FIG. 2 is a cross section of the nasal strip at section "2-2" of FIG. 1 showing the positions of the adhesive surfaces and the plastic backing of the prior art nasal strip.

FIG. 3 is a plan view of a nasal strip showing a non-adhesive covering of the central portion of the nasal strip.

FIG. 4 is a cross section at "4-4" of FIG. 3 showing a plastic covering over the adhesive surface at the central portion of the improved nasal strip.

FIG. 5 is a plan view of a non-adhesive tab member attached to the outer boundary of a right section and/or a left section of the nasal strip.

FIG. 6 is a top view of a nasal strip that has a central portion that has a width substantially equal to the end sections of the nasal strip.

FIG. 7 is a cross section of the nasal strip of FIG. 6 showing the details of the subject nasal strip tab for easy removal of the nasal strip from the person's nose.

FIG. 8 is a partial top view of a nasal strip having a semi-annular tab mounted at either or both ends of the nasal strip for easy removal of the nasal strip from a user's nose.

FIG. 9 is a cross section of the partial nasal strip of FIG. 8 showing additional details of the semi-annular tab that extends from either or both ends of the nasal strip.

DETAILED DESCRIPTION OF THE INVENTION

FIG. 1 is a plan view of a typical prior art nasal strip 10 that is used to provide improved openings of the nasal passageways particularly during sleep. The nasal strip 10 has a central portion 11, a right section 12R, and a left section 12L. A typical nasal strip 10 has a length "L" that is approximately 6 cm and a maximum width "W" that is approximately 2 cm with a length of the central portion 11 being about 2.5 cm.

FIG. 2 is a cross section of the nasal strip 10 at section "2-2" of FIG. 1. The central portion 11 of the nasal strip 10 would have a back portion 11B and an interior surface that would have an adhesive covering 11A. The right section 12R would have a back portion 12B and an interior adhesive covering 12A. The entire external portion of the nasal strip 10 would be formed from a flexible plastic material like that used for skin bandages. The entire interior surface of the nasal strip 10 would have an adhesive covering so that it would adhere to all parts of the skin on the nose onto which it would be placed.

FIG. 3 is a plan view of a nasal strip 20 that is an improved device to provide an opening of the nasal passageways particularly during sleep. The nasal strip 20 has a central portion 21 that has an interior covering 23, a right section 22R, and a left section 22L. This nasal strip 20 would also have a length that is approximately 6 cm, a maximum width "W" that is approximately 2 cm, and a length of the central portion 21 that is approximately 2.5 cm. The central portion 21 is devoid of any adhesive.

FIG. 4 is a cross section of the nasal strip 20 at section "4-4" of FIG. 3. The central portion 21 of the nasal strip 20 would have a back portion 21B and its central portion 21 would have a centrally located adhesive covering 21A onto which the interior covering 23 is attached. The right section 22R would have a back portion 22B and an interior adhesive covering 22A. The entire external portion of the nasal strip 10 would be formed from a flexible plastic material like that used for skin bandages. Unlike the prior art design as shown in FIGS. 1 and 2, the interior surface of the nasal strip 20 would not have an adhesive covering throughout its entire interior surface. For this improved design of the nasal strip 20, the central portion 21 would have the plastic covering 23 on its interior surface as is shown in FIGS. 3 and 4. This plastic covering 23 would adhere to the adhesive covering 21A of the central portion 21 of the nasal strip 20. It should also be understood that the present invention includes the concept of eliminating the coating on the central portion 21 without having the interior covering 23. This alternative design would provide several advantages of the present invention but not the increased torque that is a feature of the design of FIGS. 3 and 4.

There are four improvements in the design of the nasal strip 20 of FIGS. 3 and 4 as compared to the prior art nasal strip 10 of FIGS. 1 and 2. Firstly, the covering 23 on the interior surface of the central portion 21, increases the thickness of the central portion 21. This increased thickness of the central portion 21 provides some additional torques placed upon the left section 22L and the right section 22R when they are bent around the bridge of the nose and adhesively attached onto the sides of the nose. This increased torque is directly a result of the increased thickness of the central portion 21 of the nasal strip 20 and the absence of any adhesive on the interior surface of that central portion 21. This design provides the additional torque when the nasal strip 20 is bent around the bridge of the nose. This increased torque can provide increased openings of the left and right nasal passageways. Secondly, there is reduced discomfort upon removal of the improved design of the nasal strip 20 when it is taken off a person's nose. This is because the strongest adhesion of a nasal strip is at the center of the nose due to the fact there is typically less oil on that surface of the skin as compared to some oiliness that does typically occur at the side of a person's nose. Additionally, the fact that there is less of the skin of the nose that is covered with an adhesive automatically makes the improved nasal strip 20 removable with less discomfort. Thirdly, it is awkward to accurately place the nasal strip 10 onto the nose because it has an adhesive placed onto it entire interior surface. With the covering 23 as shown in FIGS. 3 and 4, it is much easier to hold onto the nasal strip 20 in a region where there is no adhesive, namely, the central portion 21 for more accurate placement of the nasal strip 20 onto the skin of the nose. Fourthly, to have less area of the skin on the nose that is covered with an adhesive dictates that any inflammatory skin response to that adhesive would be reduced.

In light of this analysis, it has been shown that the novel and useful nasal strip 20 as described herein would have superior characteristics as compared to a prior art nasal strip 10 that is now being marketed in many countries. It should also be understood that the present invention envisages a central portion that does not have an adhesive surface with only the end sections having those interior adhesive surfaces. This design can be accomplished without the plastic covering 23 as shown in FIGS. 3 and 4 as long as no adhesive coating is placed onto the central portion 21.

FIG. 5 shows the nasal strip or nasal dilator 20A with additional non-adhesive tabs 30 attached to outer boundaries 35L and/or 35R. of the left section 22L and the right section 22R. The tabs(s) 30 may be attached to any part of boundaries 35L and 35R and may even be secured to central portion 21 to aid a user in removal of the nasal dilator 20 from the user's nose after application. For purposes of illustration, two tabs 30 are shown in FIG. 5. However it is to be understood that only one tab 30 may be used with relation to the improved nasal dilator shown in FIG. 5.

Tabs 30 may be formed of a flexible composition such as plastic or textile material which permits the user to grasp the tab 30 for aiding the user to readily remove the nasal dilator 20A from the user's nose with a minimal amount of discomfort. Still further, either or both tabs 30 may be formed integral with the left section 32L and/or the right section 32R The particular placement of tab 30 on the outer boundary 35L or 35R and/or the central portion 21 is not important to the inventive concept as long as the tab 30 extends external to the outer edges of the nasal dilator 20A.

FIGS. 6 and 7 constitute further improvements in the design of nasal strips. Specifically, FIG. 6 is a plan view of an improved nasal strip 40 that has conventional end sections 42L and 42R but has the improvements of a wide central section 41 that is free of any adhesive and lifting tabs 43 at each end of the nasal strip 40 for easy removal of the nasal strip 40 from that person's nose. There is no known commercially available nasal strip from any manufacturer that has a central section that is the same width as the end sections of that nasal strip. The advantages of the wider central section 41 with respect to known prior art are that it is easier to place onto and remove from the nose compared to a narrow central section and it provides an additional lifting torque for the end sections 42L and 42R. Specifically, the nasal strip 40 of FIG. 6 is entirely different from a conventional skin bandage in that the central section provides a lifting torque of a least 0.1 inch-ounces onto the end sections 42L and 42R so as to produce an increased opening of the nasal passageways to improve breathing. This minimum torque can be created by using a thicker plastic for the nasal strip 40 as compared to a simple bandage or by creating multiple ridges along the length of the nasal strip 40 that could also act to increase the lifting torque for this product. Prior nasal strip designs always used narrow central sections to decrease the area of adhesive that sticks to the bridge of the nose to reduce the pain when lifting the nasal strip off of the nose, and also, the reduced area of a narrow central section limits the irritation of the skin that would occur on the bridge of the nose if a wider central section with adhesive was used. By eliminating the adhesive on the central section 41 of the nasal strip 40 and by providing a center section 41 that has the design to provide a lifting torque of at least 0.1 inch-ounces onto the end section 42L and 42R, this design provides the advantages of easier placement onto the nose, easier removal from the nose without pain or skin irritation, and due to the absence of adhesive on that central section 41, and because of it being wider and typically thicker plastic design, it provides additional lifting torque onto the end sections 42L and 42R to better open the nasal passages. Another advantage of the design of the nasal strip 40 of FIG. 6 is the center mark (or center hole) 44 that is a place for the user of this device to place his/her fingers to center that mark at the center of the bridge of the nose so that the left end section 42L and the right end section 42R will each be optimally placed onto the sides of the nose to maximize the opening of each nostril.

FIGS. 6 and 7 show two end tabs 43 attached to the external boundary 45 of the end sections 42L and 42R of the nasal strip 40. These end tabs 43 provide the advantage of making it easier to remove that nasal strip 40 from the nose. FIG. 7 shows the central section 41 (without any adhesive) and the end section 42R with an adhesive 42RA on its underside. FIG. 7 also shows that the tab 43 makes an angle "a" with the general plane of the nasal strip 40. The angle "a" could be anywhere between zero degrees to as high as 90 degrees with the optimum angle being approximately 30±20 degrees. By protruding away from the skin, the tab 43 is much easier for the person using the nasal strip 40 to pull that nasal strip 40 off from his/her skin. There is no existing nasal strip that has that improved feature.

FIGS. 8 and 9 illustrate some additional features of a nasal strip 50 that has an end tab 53 that can be placed at either or both ends of the nasal strip 50, a central section 51 that is free of any adhesive, and a right end section 52R that has an adhesive covering 52RA on its interior surface. The tab 53 is in the general shape of a semi-annulus having an outside radius R and an inside radius r. There can be some curvature of the inside border of the semi-annulus tab 53 where it meets the outer boundary of the right end section 52R as shown in FIG. 8. The width of the semi-annulus tab is given by R-r. A typical maximum radius R of the semi-annulus tab 53 is shown in FIG. 8 and it is equal to the one half the, width W of the nasal strip 50. The minimum value of the radius R would be approximately W/5. Therefore, the range of the value of R would lie between W/2 and W/5. Typical values of the width of the semi-annulus tab 53 would be a value for R-r that would be between 1 and 4 mm There is a great advantage in the design of the tab 53 of FIGS. 8 and 9 in that it has an opening 54 through which the user could place his/her thumb plus an opposing finger on that same hand to readily grab the nasal strip 50 for easy removal of the nasal strip 50 from his/her nose. No other nasal strip has that advantageous means for the easy removal of the nasal strip from that user's nose.

Although there is no angle "a" shown for the tab 53, that tab also may be positioned at an angle between zero and 90 degrees relative to the plane of the nasal strip 50.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A nasal strip for opening the nasal passageways, the nasal strip having features that include:
   an external portion that extends for the entire length of the nasal strip, the external portion being formed from a flexible plastic material, the external portion having a central section and a left end section and a right end section with the central section having a smaller width or the same width as each end section;
   an adhesive coating that covers the interior surface of each end section of the external portion of the nasal strip with the central section not having an adhesive coating on its interior surface; and
   a non-adhesive tab that extends in a generally outward direction from an external boundary of either one or both end sections of the nasal strip, the tab being attached to one or both of the right and left end sections so as to facilitate the removal of the nasal strip from the user's nose;
   wherein the tab is in the general form of a semi-annulus having an outside radius R and an inside radius r where the outside radius R has a length that is between ½ to ⅕ the width of the end sections of the nasal strip.

2. The nasal strip as recited in claim 1 where said tab extends at an angle "a" from the plane of the nasal strip wherein the angle "a" is within the approximate range of 0-90 degrees.

3. The nasal strip of claim 2 where the angle "a" is approximately 30+20 degrees from the plane of the nasal strip.

4. The nasal strip of claim 1 where the semi-annulus inner radius r and the semi-annulus outside radius R define the semi-circular tab width of R-r that is within the approximate range of 1.0 and 4.0 mm.

5. The nasal strip of claim 1 where the total length of the nasal strip including the non-adhesive tabs is approximately 8 cm.

6. The nasal strip of claim 1 where the width of the end sections of the nasal strip is approximately 2 cm.

7. The nasal strip of claim 1 where a mark or an opening is placed at the center of the central section of the nasal strip for placement of the users fingers to help guide the user in centering the central section of the nasal strip onto the center of the bridge of the nose to equalize the lifting torque on each nostril.

* * * * *